May 22, 1934. W. P. MORGAN Plant Pat. 98
FREESIA
Filed June 23, 1933
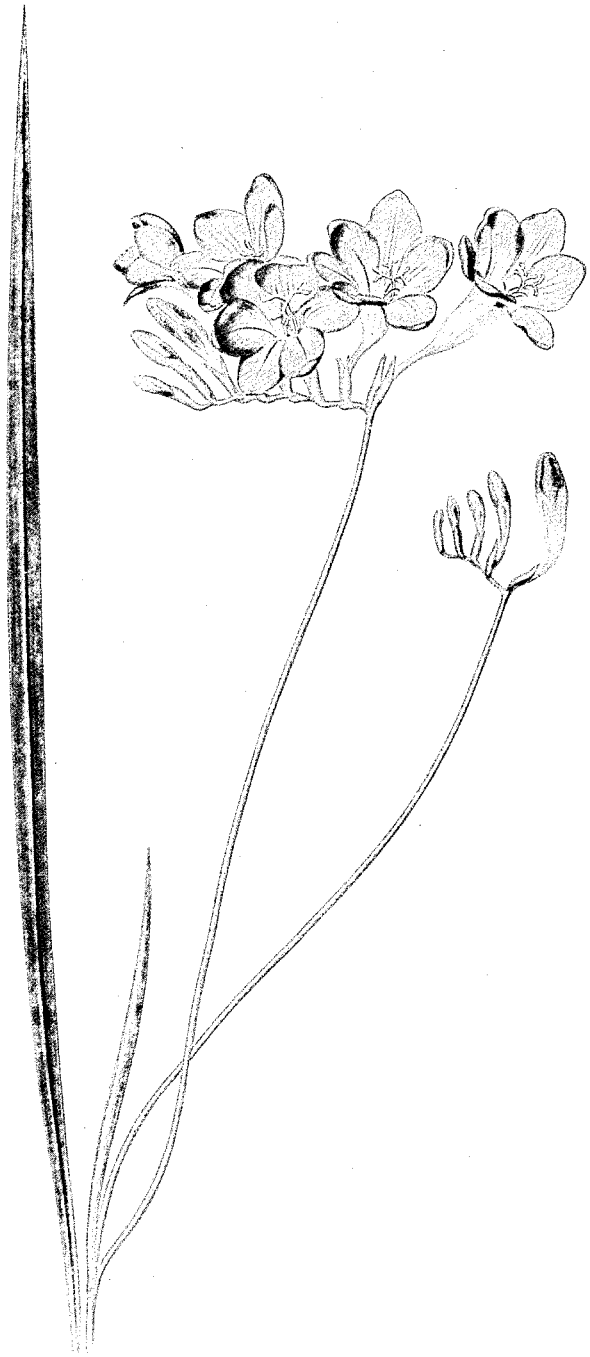
INVENTOR
W. P. Morgan
PLANT·PATENT·AGENT
Orville M. Kile Patented May 22, 1934

Plant Pat. 98

UNITED STATES PATENT OFFICE

98

FREESIA

William Pitt Morgan, Marion County, Ind., assignor to Elder and Elder Nurseries, Indianapolis, Ind., a corporation Application June 23, 1933, Serial No. 677,328

1 Claim. (Cl. 47—60)

My present invention relates to improvements in tinted or colored freesias. The object of my invention is to provide a freesia with large blossoms, a pleasing "light lavender-violet" color, tall stems sufficiently strong to hold the blossom spike upright, with dark green foliage whose tips rise to the base of the flower spike, with unusually robust constitution and other desirable and useful characters which make it suitable for florists' cut-flower use.

My new freesia was produced by the crossing of an unnamed lavender seedling of unknown parentage and Elder's Giant White. In the large size of the blossoms, upright growth and small size of the corms my improvement resembles the Elder's Giant White. After reproducing this new variety several years it was named and was awarded a gold medal by the American Society of Florists and Ornamental Horticulturists at their 1933 National Flower Show where it was displayed.

The accompanying illustration shows a spike of blossoms less than full size. The flowers on the spike have been arranged so as to portray their distinguishing characteristics of color, form, number of open blossoms, and leaf color. In order to insure accuracy in the details of color and form the artist was constantly provided with freshly cut spikes for comparison.

The following is a detailed description of this new variety of freesia:

*Plant.*—Very upright in growth, with leaves five-eighths inch in widest portion, extending upward reach to, and often above, the flower spike. The leaves are "forest green" (Ridgway's Color Standards and Nomenclature Plate XVII) to "Cossack green" (Plate VI). The lateral spikes are long and upright in growth which point is especially attractive in a freesia variety grown by commercial florists. Under good growing conditions this variety will produce spikes and foliage more than thirty-six inches in height.

*Flowers.*—The characteristic number of blossoms borne on a single terminal spike is eight, although the number may be slightly less from very small corms. The flowers of the spike are all borne in an upright position due to its axis being abruptly bent at right angles to the vertical stem or peduncle. The perianth is long, gracefully funnel-shaped. Its six segments or lobes are of nearly equal length, round at the ends and, in the fully expanded flower, open back sufficiently to expose all of the inner surface yet never reflexing. Usually four blossoms are out at one time although often the fifth blossom opens before the first begins to die. The width of the flower across the top is usually from one and one-half to two inches while the average length is two and one-half inches.

The dominant color tone is popularly described as bluish lavender. By reference to Ridgeway's Color Standards and Nomenclature, edition 1912, the dominant color of the newly opened blossom grown under normal conditions is "light lavender-violet" (Plate XXV). The three lower perianth segments are slightly darker than the upper three. In partially open blossoms these lower segments are "Bradley's violet" (Plate XXIII). The throat is lighter, becoming nearly white and blends with dull yellow in the lowest portions of the tube. The light color of the throat extends upward further on the three lower segments than on the other perianth lobes. On the inside of the lobes fine median stripes of "Bradley's violet" extend upward from the tube to blend in the color of the outermost part of the segments. The lines are more prominent on the lower segments. The slender anthers produce sufficient pollen but most of this is sterile. The colors and form here described are retained even under the most severe conditions of shipment which facts have been ascertained through careful and adequate testing.

*Bracts and bracteoles (Sepals).*—Two in number, are loose fitting, green in color and one-half inch or longer. The form and position is typical of the genus.

*Corms.*—The average size of the corms is smaller than most varieties. In this respect the variety is similar to Elder's Giant White. The variety produces as many as thirty or more cormlets from a mature corm planted the preceding August. The smallest corms produce typical blossoms.

The principal features which I believe distinguish my freesia from all other freesias are:

First, its parentage. When this variety was produced no other person or persons had access to the parent types.

Second, the distinctive "light lavender-violet" color.

Third, its large size of blossoms and large number out at one time.

Fourth, its unusual vigorous upright growth, long dark green leaves and long stems, and long lateral spikes.

Fifth, its rapidity of reproduction.

Sixth, its unusually good qualities of keeping and recovery after wilting suit it for the rigorous conditions imposed during shipment.

I claim:

The variety of freesia as shown and described, characterized particularly by its "light lavender-violet" color, large flowers, tall upright growth, wide dark green leaves and rapidity of reproduction.

WILLIAM PITT MORGAN.